United States Patent [19]

Veltman

[11] Patent Number: 4,489,535
[45] Date of Patent: Dec. 25, 1984

[54] MATERIALS AND METHOD FOR PREPARING DIALYSIS SOLUTIONS CONTAINING BICARBONATE IONS

[76] Inventor: Preston L. Veltman, 212 Old Country Rd., Severna Park, Md. 21146

[21] Appl. No.: 344,038

[22] Filed: Jan. 29, 1982

Related U.S. Application Data

[63] Continuation-in-part of Ser. No. 193,125, Oct. 2, 1980, which is a continuation-in-part of Ser. No. 123,355, Feb. 21, 1980, abandoned.

[51] Int. Cl.$^3$ .................. A61K 33/14; B65B 55/18; C09K 3/00
[52] U.S. Cl. ........................................ 53/431; 53/434; 206/524.1; 210/646; 210/647; 252/1; 252/364; 424/153
[58] Field of Search .................. 252/1; 210/646, 647; 23/313 R; 424/153; 53/431

[56] References Cited

U.S. PATENT DOCUMENTS

| | | | |
|---|---|---|---|
| 3,352,779 | 11/1967 | Austin et al. | 210/23 |
| 3,406,826 | 10/1968 | Willock | 210/87 |
| 3,515,275 | 6/1970 | Bowman | 210/22 |
| 3,560,380 | 2/1971 | Stade | 252/1 |
| 3,598,727 | 8/1971 | Willock | 210/22 |
| 3,690,340 | 9/1972 | Sipin | 137/93 |
| 3,722,680 | 3/1973 | Smith | 210/96 |
| 3,753,493 | 8/1973 | Mellor | 210/140 |
| 3,843,099 | 10/1974 | Duncan | 259/23 |
| 3,878,095 | 4/1975 | Fraiser et al. | 210/87 |
| 3,882,020 | 5/1975 | Cere | 210/85 |
| 3,920,556 | 11/1975 | Bowman | 210/321 |
| 3,962,075 | 6/1976 | Fialkoff et al. | 210/647 X |
| 4,136,708 | 1/1979 | Cosentino et al. | 137/99 |
| 4,202,760 | 5/1980 | Storey et al. | 210/22 A |
| 4,399,036 | 8/1983 | Babb et al. | 210/647 X |

FOREIGN PATENT DOCUMENTS

| | | |
|---|---|---|
| 22922 | 1/1981 | European Pat. Off. . |
| 34916 | 9/1981 | European Pat. Off. . |
| 144360 | 10/1980 | German Democratic Rep. . |
| 2025787 | 1/1980 | United Kingdom . |
| 2069855 | 9/1981 | United Kingdom . |

OTHER PUBLICATIONS

Kirkendol et al., "Potential Source of Fixed Base in Hemodialysate Solutions", vol. XXIII, Trans. Am. Soc. Artif. Intern. Organs, pp. 399–405 (1977).
Babb et al., International Publication Number WO81/03180, Nov. 12, 1981.
"Centralyte TM –Central Delivery System Bicarbonate . . . ", Two-page product bulletin by Erika Inc., One Erika Plaza, Rockleigh, N.J. 07647, Apr., 1983.
Mion et al., vol. X, Trans. Am. Soc. Artif. Int. Organs, pp. 110–113 (1964).

(List continued on next page.)

Primary Examiner—Richard D. Lovering
Attorney, Agent, or Firm—Armstrong, Nikaido, Marmelstein & Kubovcik

[57] ABSTRACT

Compositions comprising: (1) an acid-containing highly concentrated calcium salt solution which optionally can also contain magnesium ions and minor amounts of other physiologically acceptable metal ions; and (2) a particulate admixture comprising sodium bicarbonate, sodium chloride and, optionally, potassium chloride, dextrose and other physiologically acceptable materials which, in aqueous solution, are unreactive to sodium bicarbonate. Also presented is a method for preparing a dialysate comprising: (1) preparing a concentrated sodium bicarbonate solution by dissolving a particulate admixture comprising sodium bicarbonate, sodium chloride and, optionally, potassium chloride, dextrose and other physiologically acceptable materials unreactive to sodium bicarbonate in the presence of water; (2) preferably separately diluting: (a) an acid-containing highly concentrated calcium salt solution which optionally can also contain magnesium ions and minor amounts of other physiologically acceptable metal ions, and (b) the concentrated sodium bicarbonate solution; and (3) admixing the two resulting diluted solutions to form the dialysate.

17 Claims, 3 Drawing Figures

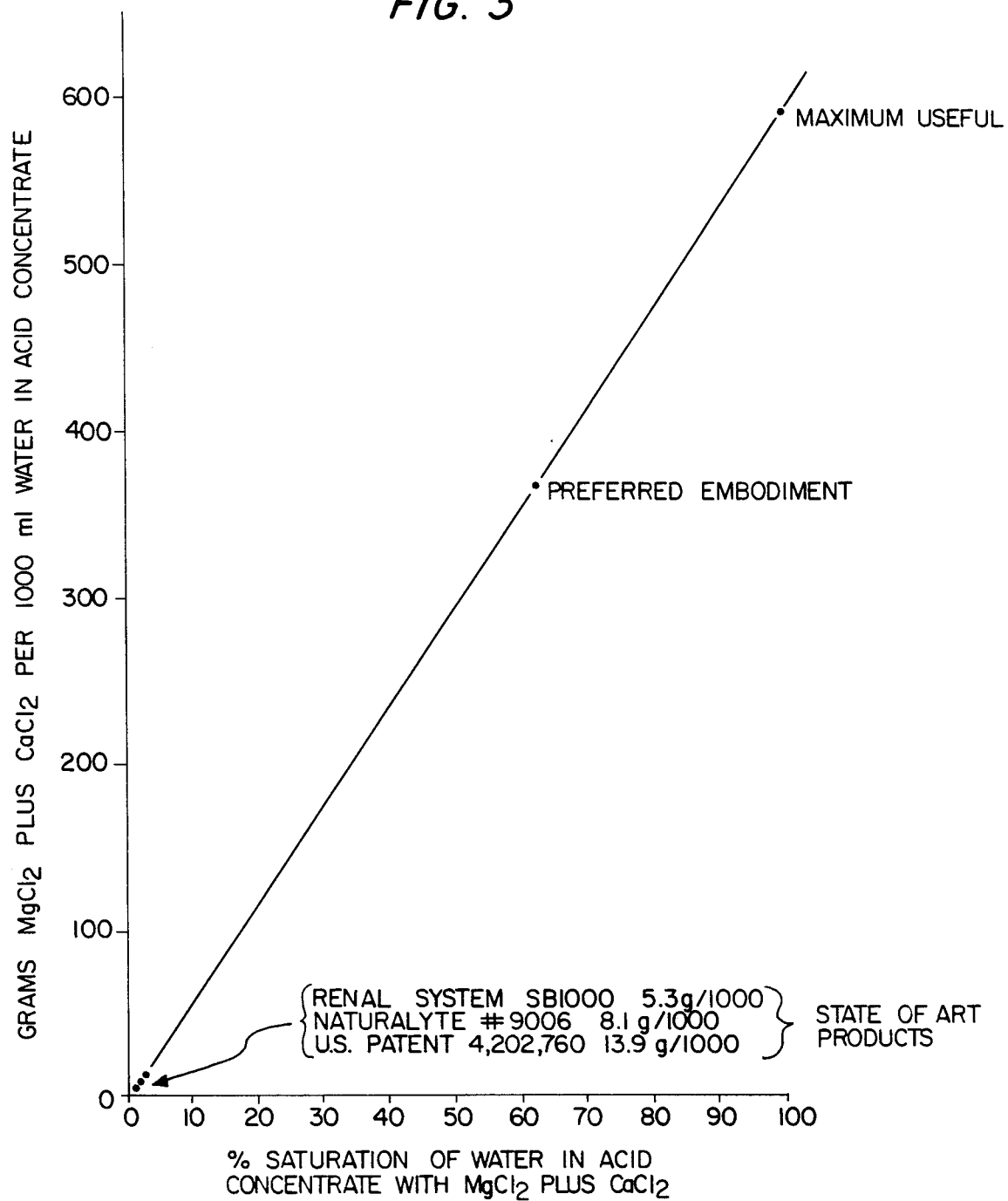

MATERIALS AND METHOD FOR PREPARING DIALYSIS SOLUTIONS CONTAINING BICARBONATE IONS

CROSS-REFERENCES TO RELATED APPLICATIONS

This is a continuation-in-part of copending application Ser. No 193,125, filed Oct. 2, 1980 and now which, in turn, is a continuation-in-part of application Ser. No. 123,355, filed Feb. 21, 1980 and now abandoned.

BACKGROUND OF THE INVENTION

This invention is in the field of hemodialysis and peritoneal dialysis and relates to improved materials and procedures for the preparation of dialysates (which are also known as "dialysis solutions" and as "dialysate solutions") comprising bicarbonate ions. The improved materials and improved methods of this invention are applicable to batch preparation of a dialysis solution and to the preparation of a dialysis solution on a continuous basis to supply a single hemodialysis machine which is also known as an "artificial kidney" (sometimes shortened to "kidney"), or to supply a plurality of such machines ("kidneys").

Patent art in the dialysis field is directed mainly towards apparatus and methods of handling dialysate solutions comprising sodium acetate as the primary alkalizing agent. The widespread use of acetate systems came about in the early 1960's when sodium acetate was commonly substituted for sodium bicarbonate as the fixed base in dialysis solutions (See Mion et al, "Substitution of Sodium Acetate for Sodium Bicarbonate in the Bath for Hemodialysis", Trans. Am. Soc. Artif. Internal Organs, 10:110, 1964).

This was done primarily because the sodium acetate-containing solutions were more stable in use in that the acetate ion does not cause calcium and magnesium ions to precipitate, whereas the available sodium bicarbonate-comprising solutions were less stable because of the low solubility of calcium and magnesium carbonates which tended to precipitate, thereby changing the ion concentration of the dialysis solution and tended to plug the semiporous membranes comprising the artificial kidney. The tendency for calcium and magnesium carbonates to precipitate at solution use concentrations caused the switch in about 1964 from sodium bicarbonate to sodium acetate as the primary alkalizing agent. This switch also made possible the use of proportioning pumps to handle dialysis solution concentrates (which, on dilution, form dialysis solutions).

Information indicating that there is "less dialysis-induced moribidity and vascular instability with bicarbonate in dialysate" is now surfacing (See, for example, Graefe et al, March, 1978 Annals of Internal Medicine, Vol. 88, No. 3 at pages 332–336). It is now apparent that bicarbonate dialysate solutions, rather than acetate solutions, are better tolerated by patients.

Prior art systems wherein dialysis solutions are prepared by admixing an acid-comprising concentrate and a bicarbonate-comprising concentrate with water are known. One such system is described in U.S. Pat. No. 4,202,760 (Storey et al). Another system is known as the Bio-Systems MAKS 400 Bicarbonate Supply Machine. Still another is known as the Drake-Willock Central Delivery System 7702. These systems are designed to use commercially available state-of-the-art acid comprising concentrates and bicarbonate-comprising concentrates as hereinafter described. It is recognized that products of this invention can be adapted for use in these systems provided specific equipment modifications and procedures are followed as hereinafter described.

The apparatus of the Storey et al patent comprises a main supply line between a water supply and the "kidney", and includes a primary recirculation loop including venturi means for mixing the dialysate concentrate with de-aerated water and, optionally, a secondary recirculation loop for preliminarily forming a dilute bicarbonate containing solution which is then fed to the primary recirculation loop for mixing with the dialysate components and supply to the "kidney". The Storey et al invention requires recirculation of a quantity of the mixed fluid through the mixing venturi in both recirculating loops in an amount which exceeds the fresh water input rate by an amount of preferably 50 to 150 percent of the fresh water intake. The preferred operating method includes the bicarbonate addition step as a partial or complete replacement for acetate in the produced hemodialysis solution.

In one example of the Storey et al patent as set forth to illustrate the best form of the invention contemplated for use in hemodialysis where all of the acetate in a normal dialysate is replaced by bicarbonate, the bicarbonate-saline concentrate of Storey et al is a mixture of 31.4 grams per liter (g/l) of NaCl and 60.6 g/l of $NaHCO_3$, and a modified dialysate acid concentrate containing 160 g/l NaCl, 5.5 g/l KCl, 8.2 g/l $CaCl_2$, 5.6 g/l $MgCl_2$ and 5.1 g/l HCl. As taught by Storey et al, the uniqueness of their apparatus for preparing dialysate for use in hemodialysis resides in the use of recirculating in-line material through a venturi used as a means to introduce concentrated solutions into the recirculating material.

The Bio-Systems MAKS 400 Bicarbonate Supply Machine comprises: (a) an acid-comprising concentrate measuring tank; (b) a bicarbonate-comprising concentrate measuring tank; (c) a solution mixing tank; (d) a water supply; (e) a dialysate supply holding tank; (f) various means for temperature control and material handling. The MAKS 400 Bicarbonate Supply Machine is designed to utilize state-of-the-art acid-comprising concentrates and bicarbonate-comprising concentrates by admixing said concentrates with water in a time sequence controlled batch manner such that, when approximately one volume of acid concentrate and two volumes of bicarbonate concentrate are mixed with water, 35 volumes of dialysate is produced.

Commercially available products, such as Naturalyte #9006, may be used in this machine. The acid concentrate of Naturalyte #9006 contains 7.149 g/l $CaCl_2$, 0.876 g/l $MgCl_2$, 2.750 g/l KCl, 185.100 g/l NaCl and 8.850 g/l acetic acid. The companion bicarbonate concentrate of Naturalyte #9006 is made by dissolving a particulate admixture of sodium bicarbonate (626 grams) and sodium chloride (221 grams) to form a bicarbonate concentrate containing 24.715 g/l NaCl and 70.006 g/l $NaHCO_3$.

The Drake-Willock Central Delivery System 7702 comprises interconnected reciprocating proportioning pump means to admix an acid-containing concentrate and a bicarbonate-comprising concentrate with water to produce dialysate. This equipment is designed to use products such as marketed by Renal Systems, Inc. under the tradename of BC-1 SB-1000 Bicarbonate System. This bicarbonate concentrate contains 23.59 g/l NaCl and 66.03 g/l NaHCO$_3$. For single patient use, requiring 190 liters dialysate per patient, a bicarbonate-comprising concentrate is made by dissolving the contents of the marketed BC-1 Bicarbonate Concentrate Powder containing 223 grams NaCl and 624 grams NaHCO$_3$ in 2.5 gallons of water (9.45 liters). The companion SB-1000 aqueous acid concentrate marketed contains 3.85 g/l CaCl$_2$, 1.42 g/l MgCl$_2$, 2.96 g/l KCl, 91.85 g/l NaCl and 4.82 g/l acetic acid. When 9.45 liters of this acid concentrate and 9.45 liters of the aforementioned bicarbonate concentrate are proportionately admixed with 171 liters of water, 190 liters of dialysate is produced.

Recent patent art dealing with apparatus and method for preparing a hemodialysis solution, optionally containing bicarbonate, is reviewed in the aforesaid U.S. Pat. No. 4,202,760 to Storey et al issued May 13, 1980. U.S. Pat. Nos. 3,515,275 and 3,920,556 and patents cited therein describe the use of positive displacement piston pumps in continuous dialysate supply systems for a single artificial kidney. Other patents relating thereto include: U.S. Pat. Nos. 3,406,826, 3,598,727 and 3,878,095. These patents disclose double-acting piston and cylinder units or variable output positive displacement pumps which are mechanically adjustable for controllable response to measurement of conductivity or dialysate component concentrations to adjust the product solution (dialysate) concentrate to pre-set, predetermined limits. Additional patents which should be considered to place the present invention in proper perspective include U.S. Pat. Nos 3,352,779; 3,690,340, 3,722,680; 3,753,493; 3,843,099 and 3,882,020.

SUMMARY OF THE INVENTION

This invention provides, at a relatively low cost, improved material formulations and an improved method for preparing bicarbonate comprising solutions for dialysis use. The materials include, in each instance: (1) a highly concentrated acidic solution which I prefer to call "an acidic concentrated aqueous solution" or "an acidic concentrated first aqueous solution". Said solution comprises physiologically acceptable (or suitable) calcium salts in a predetermined amount and, optionally, a suitable magnesium salt in a predetermined calcium-to-magnesium ratio and a specific amount of a physiologically acceptable acid to obtain a pH of the final dialysis solution between 7.2 and 7.4; and (2) a particulate product comprising or consisting essentially of NaHCO$_3$, NaCl and, optionally, KCl, in predetermined ion ratios (or concentrations) and, also optionally, dextrose. The preferred method for preparing such dialysis solutions comprises: (1) forming a bicarbonate comprising aqueous concentrate by dissolving said particulate product in water; (2) preferably separately diluting the highly concentrated solution comprising calcium and said bicarbonate comprising aqueous concentrate to form two diluted solutions, each of said diluted solutions having a volume which is about ½ of the final dialysis solution volume; and (3) concurrently admixing the two aforesaid diluted solutions to form the final dialysis solution for use in hemodialysis or peritoneal dialysis.

The aforesaid highly concentrated acid solution (the acidic concentrated aqueous solution) of the instant invention contains all of the acid, all of the calcium salt and all of the magnesium salt used in formulating the dialysis solutions of said invention. Said acidic acid concentrated aqueous solution is free of sodium chloride and sodium bicarbonate.

All of the sodium bicarbonate and all of the sodium chloride, plus all of the potassium chloride (where present) and all of the dextrose (where present) which are used for the dialysis solutions of the instant invention are provided by a second aqueous solution which is prepared from a substantially waterfree particulate admixture (or particulate admixture product) which contains all of said sodium bicarbonate, said sodium chloride, said potassium chloride and said dextrose.

BRIEF DESCRIPTION OF THE DRAWINGS

FIG. 3 illustrates how the concentrates of this invention differ from those of the prior art.

DESCRIPTION OF PREFERRED EMBODIMENTS

Figure 1:
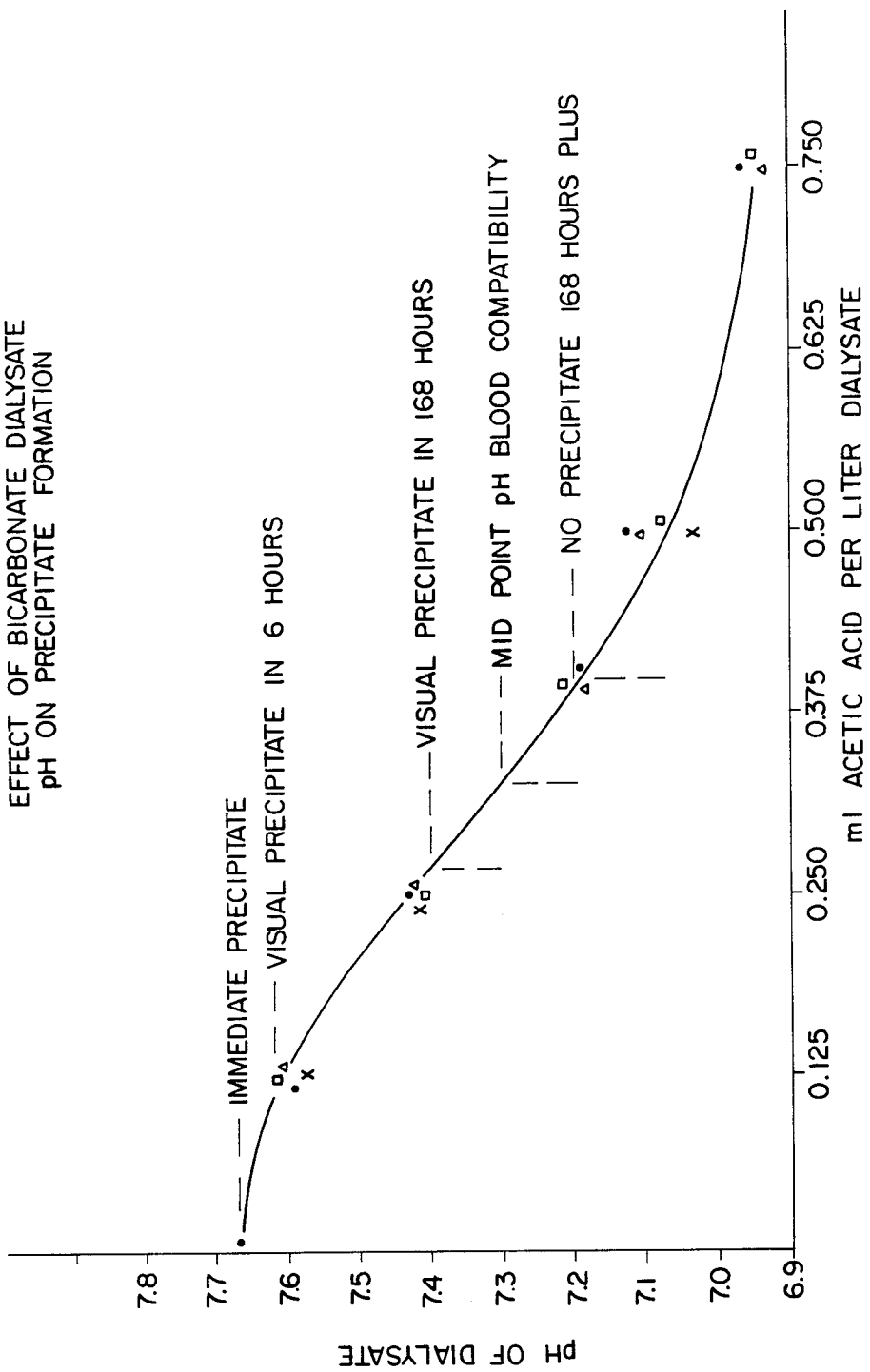
FIG. 1 illustrates the effect of pH on bicarbonate containing dialysate stability against precipitate formation.

The instant invention will be better understood by referring to the following specific but nonlimiting examples. It is understood that said invention is not limited by these examples which are offered merely as illustrations. It is also understood that modifications can be made without departing from the spirit and scope of the invention.

EXAMPLE 1

A quantity of a calcium ion, magnesium ion and chloride ion-comprising acid concentrate, and a quantity of a bicarbonate ion, sodium ion and potassium ion-comprising concentrate, formulated to produce by admixture with water 180 liters of dialysis solution (dialysate) containing, in milli-equivalents per liter (mEq per liter): $Na^+$, 137; $K^+$, 2; $Ca^{+2}$, 3; $Mg^{+2}$, 1.5; $HCO_3^-$, 36; $Cl^-$, 107.5 were made as follows:

Acid Concentrate Preparation:

199.8 grams of CaCl$_2$, 85.7 grams of MgCl$_2$ and 77.99 grams of hydrochloric acid were dissolved in water to a volume of one liter. One hundred fifty (150) cubic centimeters of this concentrate (the resulting acid concentrate) is sufficient to supply the magnesium ions, the calcium ions and a portion of the chloride ions required in the foregoing dialysate formulation.

Bicarbonate Concentrate Preparation:

A unit package, the contents of which when dissolved in water will supply the bicarbonate ion, the potassium ion, the sodium ion and the balance of the chloride ion required in the foregoing 180 liters of dialysis solution (dialysate formulation), was prepared by admixing 1,062.9 grams of sodium chloride, 544.45 grams of sodium bicarbonate and 26.85 grams of potassium chloride. This unit package was dissolved in water to a volume of 9 liters to form a bicarbonate comprising concentrate (an aqueous solution consisting essentially of all the sodium ions and all the bicarbonate ions present in the dialysis solution of this example).

When the foregoing acid concentrate in the amount of 150 cc volume and the bicarbonate comprising concentrate in the amount of 9 liters was admixed with 170.85 liters of water, a dialysis solution having the foregoing composition was formed.

EXAMPLE 2

A quantity of a calcium ion, magnesium ion, chloride ion and acetate ion-comprising acid concentrate and a quantity of sodium ion, potassium ion, bicarbonate ion and chloride-comprising concentrate sufficient to produce, by admixing with water, 180 liters of dialysate containing in milli-equivalents per liter: $Na^+$, 148.2; $K^+$, 1.0; $Ca^{+2}$, 3.5; $Mg^{+2}$, 0.5; $Cl^-$, 111.86; $HCO_3^{31}$, 41.39; $Ac^-$ (acetate), 4.0, was made as follows:

Acid Concentrate Preparation:

232.6 grams of $CaCl_2$, 28.5 grams of $MgCl_2$ and 287.92 grams of acetic acid were dissolved in water to a volume of one liter. One hundred fifty cubic centimeters of this concentrate is sufficient to supply the calcium ions, the magnesium ions, the acetate ions and a portion of the chloride ions required in the foregoing 180 liters of dialysate formulation.

Bicarbonate Concentrate Preparation:

A unit package, the contents of which was dissolved in water to a volume of 12.85 liters to prepare the bicarbonate concentrate was prepared by admixing 1,124.37 grams of sodium chloride, 625.99 grams of sodium bicarbonate and 13.42 grams of potassium chloride. The 12.85 liters of this bicarbonate-comprising concentrate will supply all of the sodium ions, the potassium ions, the bicarbonate ions and the balance of the chloride ions required in the dialysis solution of this Example.

When the foregoing acid concentrate in 150 cc volume and the bicarbonate-comprising concentrate in 12.85 liters volume were admixed with 167 liters of water, 180 liters of a dialysis solution having the foregoing composition was formed.

EXAMPLE 3

A quantity of a calcium ion, magnesium ion, chloride ion and acetate ion-containing concentrate, and a quantity of sodium ion, potassium ion, bicarbonate ion and chloride ion-containing concentrate sufficient to produce, by admixture with water, 180 liters of dialysate, containing in milli-equivalents per liter: $Na^+$, 137.1; $K^+$, 1.97; $Ca^{+2}$, 3.46; $Mg^{+2}$ 1.48; $HCO_3^-$, 39.1; $Cl^-$, 105.16; $Ac^-$, 5.0, was made as follows:

Acid Concentrate Preparation:

237.07 grams of $CaCl_2$, 84.73 grams of $MgCl_2$ and 360 grams of acetic acid were dissolved in water to a volume of one liter. One hundred fifty cubic centimeters of this concentrate is sufficient to supply the calcium ions, the magnesium ions, the acetate ions and a portion of the chloride ions in the foregoing 180 liters of dialysate formulation.

Bicarbonate Concentrate Preparation:

A unit package, the contents of which was dissolved in water to a volume of 12.85 liters to prepare the bicarbonate concentrate of this example, was prepared by admixing 1,033.49 grams of NaCl, 591.12 grams of $NaHCO_3$ and 26.50 grams of KCl. The 12.85 liters of this concentrate will supply all of the sodium ions, the potassium ions, the bicarbonate ions and the balance of the chloride ions required in the dialysis solution of this Example.

When the foregoing 150 cc of acid concentrate and the 12.85 liters of bicarbonate concentrate were admixed with 167 liters of water, 180 liters of a dialysis solution having the foregoing composition was formed.

EXAMPLE 4

A quantity of a calcium ion, magnesium ion, chloride ion and acetate ion-containing concentrate and a quantity of sodium ion, potassium ion, bicarbonate ion and chloride ion-containing concentrate sufficient to produce, by admixture with water, 180 liters of dialysate containing in milli-equivalents per liter: $Na^+$, 137.3; $K^+$, 1.97; $Ca^{+2}$, 1.7; $Mg^{+2}$, 0.37; $Cl^-$, 105.2; $HCO_3^-$, 39.1; $Ac^-$, 5.1, was made as follows:

Acid Concentrate Preparation:

113.08 grams of $CaCl_2$, 21.11 grams of $MgCl_2$ and 365 grams of acetic acid were dissolved in water to a volume of one liter. One hundred fifty cubic centimeters of this concentrate is sufficient to supply the calcium ions, the magnesium ions, the acetate ions and a portion of the chloride ions required in the foregoing 180 liters of dialysate formulation.

Bicarbonate Concentrate Preparation:

A unit package, the contents of which was dissolved in water to a volume of 12.85 liters to prepare a bicarbonate-comprising concentrate, was prepared by admixing 1,033.17 grams of sodium chloride, 591.33 grams of sodium bicarbonate and 26.44 grams of potassium chloride. The 12.85 liters of this concentrate is sufficient to supply all of the sodium ions, the potassium ions, the bicarbonate ions and the balance of the chloride ions required in the dialysis solution of this Example.

When 150 ml of the foregoing acid concentrate and 12.85 liters of the bicarbonate concentrate were admixed with 167 liters of water, a dialysate solution having the foregoing composition was produced.

EXAMPLE 5

A quantity of a calcium ion, magnesium ion, chloride ion, and acetate ion-containing concentrate and a quantity of sodium ion, potassium ion, bicarbonate ion and chloride ion-containing concentrate sufficient to produce, by admixture with water, 180 liters of dialysate containing in milli-equivalents per liter: $Na^+$, 135; $K^+$, 1.5; $Ca^{+2}$, 2.5; $Mg^{+2}$, 1.0; $Cl^-$, 101.9; $HCO_3^-$, 38; $Ac^-$, 5, was made as follows:

Acid Concentrate Preparation:

166.45 grams of $CaCl_2$, 57.13 grams of $MgCl_2$ and 360.23 grams of acetic acid were dissolved in water to a volume of one liter. One hundred fifty cubic centimeters of this concentrate is sufficient to supply the calcium ions, the magnesium ions, the acetate ions and a portion of the chloride ions required in the foregoing 180 liters of dialysate.

Bicarbonate Concentrate Preparation:

A unit package, the contents of which was dissolved in water to a volume of 12.85 liters to form the bicarbonate concentrate, was prepared by admixing 1,020.1 grams of sodium chloride, 574.7 grams $NaHCO_3$ and 20.13 grams of KCl. The 12.85 liters of this concentrate is sufficient to supply all of the sodium ions, the potassium ions, the bicarbonate ions and the balance of the chloride ions required in the dialysate solution of this Example.

When 150 ml of the foregoing acid concentrate and 12.85 liters of the bicarbonate concentrate were admixed with 167 liters of water, 180 liters of a dialysis solution having the foregoing composition was formed.

EXAMPLE 6

A quantity of a calcium ion, chloride ion and acetate ion-containing concentrate and a quantity of sodium ion, potassium ion, bicarbonate ion and chloride ion-containing concentrate sufficient to product, by admixture with water, 180 liters of dialysate containing in milli-equvalents per liter: Na+, 137.3; K+, 1.97; Ca+2, 1.7; Mg+2, 0; Cl−, 102; HCO3−, 39.1; Ac−, 5.1, was made as follows:

Acid Concentrate Preparation:

113.08 grams of CaCl2 and 365 grams of acetic acid were dissolved in water to a volume of one liter. One hundred fifty cubic centimeters of this concentrate is sufficient to supply the calcium ion, the acetate ion and a portion of the chloride ions required in the foregoing 180 liters of dialysate formulation.

Bicarbonate Concentrate Preparation:

A unit package, the contents of which was dissolved in water to a volume of 12.85 liters to prepare a bicarbonate-comprising concentrate, was prepared by admixing 1,033.17 grams of NaCl, 591.33 grams of NaHCO3 and 26.44 grams of KCl. The 12.85 liters of this concentrate is sufficient to supply all of the sodium ion, the potassium ions, the bicarbonate ions and the balance of the chloride ions required in the dialysis solution of this Example.

When 150 ml of the foregoing acid concentrate and 12.85 liters of the bicarbonate concentrate were admixed with 167 liters of water, 180 liters of a dialysis solution having the foregoing composition was formed.

EXAMPLE 7

A quantity of a calcium ion, magnesium ion, chloride ion and acetate ion-containing concentrate and a quantity of sodium ion, bicarbonate ion and chloride ion-containing concentrates sufficient to produce, by admixture with water, 180 liters of dialysate solution containing in milli-equivalents per liter: Na+, 137.3; K+, 0; Ca+2, 1.7; Mg+2, 0.37; Cl−, 100.3; HCO3−, 39.1; Ac−, 4.4, was made as follows:

Acid Concentrate Preparation:

113.08 grams of CaCl2, 21.11 grams of MgCl2 and 315 grams of acetic acid were dissolved in water to a volume of one liter. One hundred fifty cc of this concentrate is sufficient to provide the calcium ion, the magnesium ion, the acetate ion and a portion of the chloride ions required in the foregoing 180 liters of dialysate formulation.

Bicarbonate Concentrate Preparation:

A unit package, the contents of which was dissolved in water to a volume of 12.85 liters to prepare a bicarbonate concentrate, was prepared by admixing 1,033.17 grams of NaCl and 591.33 grams of NaHCO3. The 12.85 liters of this concentrate is sufficient to supply all of the sodium ion, the bicarbonate ions and the balance of the chloride ions required in the dialysis solution of this Example.

When the foregoing acid concentrate in the amount of 150 cc and the 12.85 liters of the bicarbonate-comprising concentrate were admixed with 167 liters of water, 180 liters of a dialysis solution having the foregoing composition was formed.

EXAMPLE 8

A quantity of a calcium ion, magnesium ion, chloride ion and acetate-containing concentrate, essentially saturated with respect to calcium chloride and magnesium chloride with regard to water present, and a quantity of sodium ion, potassium ion, bicarbonate ion and chloride ion-containing concentrate sufficient to produce, by admixture with water, 180 liters of dialysate containing in milli-equivalents per liter: Na+, 148.2; K+, 1.0; Ca+2, 3.5; Mg+2, 0.5; Cl−, 111.86; HCO3−, 41.39; Ac−, 4.4, was made as follows:

Acid Concentrate Preparation:

34.89 grams of CaCl2 and 4.28 grams of MgCl2 were dissolved in 66.5 grams of water forming, at 20° C., a saturated solution with respect to calcium chloride and magnesium chloride. To this solution was added 47.2 grams of acetic acid. The solution weighed 153.87 grams. This quantity of acid concentrate is sufficient to supply the calcium ions, the magnesium ions, the acetate ions and a portion of the chloride ions required in the foregoing 180 liters of dialysate formulation.

Bicarbonate Concentrate Preparation:

A unit package, the contents of which was dissolved in water to a volume of 12.85 liters to prepare the bicarbonate concentrate was prepared by admixing 1,124.47 grams of NaCl, 626 grams of NaHCO3 and 13.42 grams of KCl. The 12.85 liters of this bicarbonate comprising concentrate will supply all the sodium ions, the potassium ions, the bicarbonate ions and the balance of the chloride ions required in the dialysis solution of this Example.

When the foregoing acid concentrate, in weight 153.87 grams, and the bicarbonate concentrate in 12.85 liters volume were mixed with 167 liters of water, 180 liters of a dialysate solution having the foregoing composition was formed.

EXAMPLE 9

A quantity of a calcium ion, magnesium ion, chloride ion and acetate ion-containing concentrate and a quantity of sodium ion, potassium ion, bicarbonate ion, chloride ion and dextrose-containing concentrate sufficient to produce, by admixture with water, 180 liters of dialysate containing in milli-equivalents per liter: Na30, 148.2; K+, 1.0; Ca+2, 3.5; Mg+2, 0.5; Cl−, 111.86; HCO3−, 41.39; Ac−, 4.0; dextrose 2 g/l, was made as follows:

Acid Concentrate Preparation:

232.6 grams of CaCl2, 28.5 grams of MgCl2 and 287.92 grams of acetic acid were dissolved in water to a volume of one liter. One hundred fifty cubic centimeters of this concentrate is sufficient to supply the calcium ions, the magnesium ions, the acetate ions and a portion of the chloride ions required in the foregoing dialysate formulation.

Bicarbonate Concentrate Preparation:

A unit package, the contents of which were dissolved in water to a volume of 12.85 liters to prepare the bicarbonate concentrate, was prepared by admixing 1,124.37 grams of sodium chloride, 625.99 grams of sodium bicarbonate, 13.42 grams of potassium chloride and 360 grams of dextrose. The 12.85 liters of this concentrate will supply all of the sodium ions, the potassium ions, the bicarbonate ions, the dextrose and the balance of the chloride ions required in the dialysis solution or dialysate formulation of this Example.

When 150 ml of the foregoing acid concentrate and 12.85 liters of the bicarbonate concentrate were admixed with 167 liters of water, 180 liters of a dialysis solution having the foregoing composition was formed.

EXAMPLE 10

A quantity of a calcium ion, magnesium ion, chloride ion and lactate ion-containing concentrate and a quantity of sodium ion, potassium ion, bicarbonate ion, chloride ion and dextrose-containing concentrate sufficient to produce, by admixture with water, 180 liters of dialysate containing in milli-equivalents per liter: $Na^+$, 132; $Cl^-$, 83.3; $HCO_3^-$, 39; $Ca^{+2}$, 3.5; $Mg^{+2}$, 1.5; lactate$^-$, 3.5; and 1.5% by weight of dextrose, was made as follows:

Acid Concentrate Preparation:

233.07 grams of calcium chloride, 85.71 grams of magnesium chloride and 378.34 grams of lactic acid were dissolved in water to a volume of one liter. One hundred fifty cubic centimeters of this concentrate is sufficient to supply the calcium ions, the magnesium ions, the lactate ions, and a portion of the chloride ions required in the foregoing 180 liters of dialysate formulation.

Bicarbonate Concentrate Preparation:

A unit package, the contents of which was dissolved in water to a volume of 12.85 liters to prepare the bicarbonate concentrate, was prepared by admixing 589 grams of sodium bicarbonate, 823.79 grams of sodium chloride and 2,700 grams of dextrose. The 12.85 liters of this concentrate will supply all of the sodium ions, the bicarbonate ions, the dextrose and the balance of the chloride ions required in the dialysis solution of this Example.

When 150 ml of the foregoing acid concentrate and 12.85 liters of the bicarbonate concentrate were admixed with 167 liters of water, 180 liters of a dialysis solution having the foregoing composition was formed.

EXAMPLE 11

A quantity of a calcium ion, magnesium ion, chloride ion and lactate ion-containing concentrate and a quantity of a particulate mixture consisting essentially of sodium chloride, sodium bicarbonate and dextrose which, when admixed with sufficient water produce two liters of a peritoneal dialysate containing in milli-equivalents per liter: $Na^+$, 132; $Cl^-$, 83.3; $HCO_3^-$, 39; $Ca^{+2}$, 3.5; $Mg^{+2}$, 1.5; lactate$^-$, 3.5; and 1.5% by weight dextrose was made as follows:

Acid Concentrate Preparation:

1.666 cubic centimeters of acid concentrate as prepared in Example 10 was placed in a hypodermic needle equipped syringe.

Bicarbonate Concentrate Preparation:

45.7 grams of a bicarbonate-comprising particulate unit package, as prepared in Example 10, was placed in a flexible plastic bag and the air removed therefrom.

The dialysate solution of this Example, which is well adapted for use in peritoneal dialysis, was prepared by first introducing two liters of de-aerated water into the flexible plastic bag. Solution of the bicarbonate-comprising particulate was accomplished by physical movement of the bag for about two minutes. The acid concentrate was then introduced and admixed with the contents of the bag for one minute to produce the aforesaid 2 liters of the peritoneal dialysate of this Example.

FIG. 1 illustrates the effect of pH on the tendency of bicarbonate-comprising dialysates having the composition described in Example 2 to form precipitates. The several experimental points plotted in said Figure represent a series of identically prepared dialysate solutions, with the exception of the amount of glacial acetic acid added per liter of dialysate to control the pH of the solution. To be compatible with blood, the dialysate solution must have a pH between about 7.2 and 7.4. In this series of Experiments, using 0.25 ml of glacial acetic acid per liter, a pH of 7.4 was obtained and, after some 168 hours standing at room temperature, precipitate formation in the form of readily observed light-reflecting particles was observed.

A similar preparation, but containing 0.125 cc glacial acetic acid per liter and having a pH of 7.57, developed a similar visual precipitate within six hours, while another similar preparation to which no acetic acid was added had a pH of 7.65 and a precipitate of magnesium and calcium carbonates formed immediately.

Preparations containing 0.375 cc and more of glacial acetic acid showed no evidence of precipitate formation for over 168 hours. FIG. 1 illustrates the criticality of pH insofar as it relates to precipitate formation in magnesium and calcium-comprising bicarbonate dialysate solutions, and said FIG. 1 directionally can be used for product formulation purposes.

Figure 2:
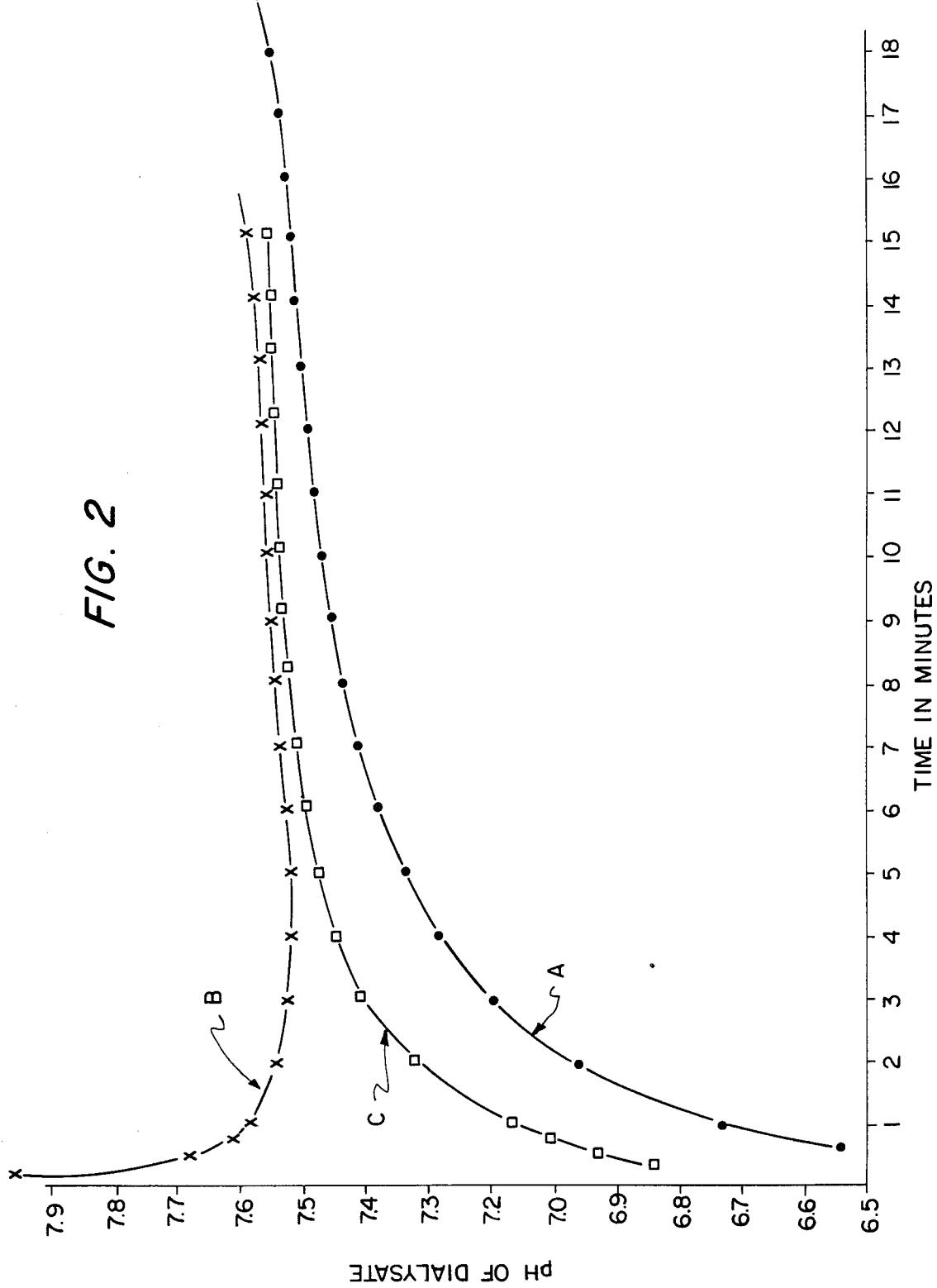
FIG. 2 illustrates how pH varies with composition-wise identical dialysis solutions differing only in order and manner of diluting the components before admixing.

When acid concentrates (for example, acetic acid-containing concentrates) of this invention are admixed with aqueous solutions comprising sodium bicarbonate, the acid, in part, reacts with the sodium bicarbonate to form sodium acetate, hydrogen ion, and bicarbonate ion. As time passes, under use conditions, there is a tendency for the bicarbonate ion to dissociate with the loss of $CO_2$ from the solution, causing an increase in pH and a loss of bicarbonate ion content in the dialysis solution as illustrated in FIG. 2. Because of this fact, it is necessary for pH control to include sufficient acid in the acid concentrate to compensate for that acidity which is lost by $CO_2$ evolution from the time of acid concentrate admixture with the bicarbonate-comprising solution under use conditions.

The formulation of Example 2 is given to ilustrate how, in practice, the amount of acid used in concentrate formulation can be varied to achieve control of dialysate pH to avoid undesirable calcium and magnesium precipitation. The dialysate produced following the teaching of Example 2 had a pH value of near 7.4 when 287.92 grams acetic acid per liter was contained in the acid concentrate.

Following the teaching of FIG. 1, in order to produce a dialysate having a pH of near 7.3 several hours after admixing the acid concentrate and the bicarbonate solution, it would be necessary to use 393.28 grams per liter acetic acid in the acid concentrate of Example 2. In practice, the exact acid content of the acid concentrate, e.g., acetic, lactic, hydrochloric or other physiologically acceptable acids, is selected and controlled to obtain the required dialysate pH at time of use.

In the development of this invention, it was found that the extent of component dilution and order of admixing is important, insofar as obtained dialysate stability properties are concerned. FIG. 2 illustrates how the pH varies with time in composition-wise, identical dialysate preparations (solutions), differing only in the manner and order of diluting the components before admixing. Experimentally, pH was measured using a meter sensitive to 0.01 pH unit. Standard buffer solutions were used for calibration. The dialysate solutions were contained in a 500 ml beaker and mixed, using a 1½" magnetic bar rotating at about 600 rpm (kept constant for all experiments). Stirring energy was sufficient to form a vortex down to the magnet bar. The following procedure was used:

Curve A of FIG. 2

(1) 0.416 ml of Example 2 calcium, magnesium ion-comprising concentrate placed in 500 ml beaker.
(2) 463.9 ml distilled water added and stirring initiated; pH noted.

(3) 35.7 ml of Example 2 bicarbonate solution concentrate added and change in pH noted from time zero.

Curve B of FIG. 2

(1) 35.7 ml of Example 2 bicarbonate solution concentrate placed in 500 ml beaker.
(2) 463.9 ml distilled water added and stirring initiated; pH noted.
(3) 0.416 ml Example 2 calcium, magnesium ion concentrate solution added and change in pH noted from time zero.

Curve C of FIG. 2

(1) 0.416 ml Example 2 calcium, magnesium ion-comprising concentrate admixed with 249.6 ml distilled water.
(2) 35.7 ml of Example 2 bicarbonate-comprising concentrate admixed with 214.3 ml distilled water.
(3) Solutions (1) and (2) above concurrently poured into 500 ml beaker with stirrer rotating. pH change observed as a function of time.

The acetic acid content of the dialysate solutions depicted in FIG. 2 were intentionally selected to have a final pH near 7.4 so as to better observe the onset of visual calcium and magnesium carbonate precipitate formation. It was surprisingly found that when, at the time of initiating mixing, the bulk of the solution was acid and the concentrated bicarbonate was introduced into the system, the approach to a steady state pH condition was relatively slow (Curve A) as compared to the situation where the bulk of the solution was basic (Curve B) and the acid concentrate was added. The small volume of acid concentrate, when added to the bulk of basic solution, caused a far more rapid change in pH than was observed for Curve A.

Curve C of FIG. 2 represents the situation where the acid components and the basic components are diluted to equal volume before admixing. It was found that this procedure produces a more stable dialysate solution as was observed by noting the longer time before the onset of visual precipitation. Visual precipitation was not observed until about 168 hours, whereas the precipitate for Systems A and B were noted in about 48 hours.

The rate and amount of $CO_2$ evolution was observed to differ for procedures A, B and C. When, as in Curve B of FIG. 2, acid concentrate was added to a bulk of diluted bicarbonate, $CO_2$ evolution was visually initially noticeably greater than when bicarbonate concentrate is added to a diluted acid solution as in curve A of FIG. 2.

It was also noted that visually observable $CO_2$ evolution continued for a longer period of time when, as in Curve A, concentrated bicarbonate was admixed with diluted acid. Tests represented by Curve C of FIG. 2 had less $CO_2$ evolution, as indicated by $CO_2$ evolution and pH change, than either tests represented by Curve A or Curve B. The pH measurements of Curve C indicate that a relatively steady state was reached after about fifteen minutes, whereas tests represented by both Curves A and B continued to show noticeable increases in pH after about 15 minutes.

Applicant has found that bicarbonate-comprising dialysate solutions of improved stability against precipitation formation can be made by separately diluting an aqueous concentrated magnesium, calcium and acid-comprising component, and a concentrate comprising sodium bicarbonate, sodium chloride and potassium chloride with water, each to about one-half of the total volume of the final dialysate solution (see FIG. 2, Curve C) before concurrently admixing the two diluted materials, preferably in turbulent flow, to form the desired dialysate solution having a predetermined pH of between 7.2 and 7.4. The aforementioned procedure can be conducted on a batch or on a continuous in-line basis.

Applicant does not wish to be bound by theory. However, it is known that, in all mixing systems, it is difficult to uniformly disperse a small volume of liquid or solid concentrated material effectively throughout a large volume of diluent. As one "predilutes" a given volume of concentrated material with a portion of the diluent, before admixing with the remainder of the diluent, the net resulting uniformity of the solution (under any given admixing procedure) is improved. Thus, the extent of individual component pre-dilution can be utilized to improve solution quality where incremental volume ion concentrates are important.

FIG. 3 illustrates how the acid concentrates of this invention differ from those of the prior art from the standpoint of contained calcium chloride plus magnesium chloride per liter of water in the acid concentrate (acidic concentrated aqueous solution). Currently used commercial acid concentrates, for example, contain from 5.3 to 13.87 grams of calcium chloride plus magnesium chloride per liter of water, whereas a preferred acid concentrate of this invention contains 366.4 grams of calcium chloride plus magnesium chloride, if present. Further, Example 8 foregoing, demonstrates that near-saturated concentrates, such as one containing 589 grams calcium chloride, have unique utility. Expressed in terms of percent saturation of water contained in the acid concentrate products of prior art, which are less than 2% saturated, preferred composition of this invention are 60 or more percent saturated.

Acid concentrates of this invention differ markedly from prior art materials from the composition and concentration standpoints and have operational and economical advantages.

The foregoing evidence demonstrates that the unique, highly concentrated acid-containing calcium ion and, optionally, magnesium ion-comprising compositions of this invention and the unique particulate sodium bicarbonate-comprising compositions can be utilized using a wide range of solution admixing procedures, but that a preferred procedure is one wherein a maximum dilution of each component is obtained before admixing the bicarbonate-comprising solution with solutions comprising ions reactive to bicarbonate. Such ions include calcium ions and magnesium ions.

The dialysis solutions of this invention are, as is conventional in the art, preferably prepared with de-aerated water.

As used herein, the term "cc" means "cubic centimeter" and, for the purpose of this invention, 1 cc is equivalent to 1 ml (one milliliter).

What is claimed:

1. A method for preparing a bicarbonate dialysis solution, said dialysis solution consisting essentially of: (a) about 120 to 155 m Eq per liter of sodium ions; (b) about 30 to 42 m Eq per liter of bicarbonate ions; (c) about 1 to 5 m Eq per liter of calcium ions; (d) about 80 to 115 m Eq per liter of chloride ions; and (e) water to make one liter, said dialysis solution being prepared by admixing: (A) an acidic concentrated first aqueous solution consisting essentially of an amount of calcium chloride effective for providing about 1 to 5 m Eq of calcium ions per liter of said dialysis solution and an amount of a physiologically acceptable acid effective for causing said dialysis solution to have a pH of 7.2 to 7.4, said acidic concentrated first aqueous solution being free of sodium chloride; and (B) a second aqueous solution consisting essentially of all of the sodium ions and all of the bicarbonate ions present in said dialysis solution and being free of calcium and magnesium salts, said acidic concentrated first aqueous solution and said second aqueous solution being admixed with water to form said dialysis solution.

2. The method of claim 1 in which 0 to 115 grams per liter of magnesium chloride is present in the acidic concentrated first aqueous solution.

3. The method of claim 1 in which the physiologically acceptable acid is a member selected from the group consisting of acetic acid, lactic acid and hydrochloric acid.

4. The method of claim 1 in which an amount of potassium chloride effective for providing 0 to 3 m Eq of potassium ions per liter of said dialysis solution is present in said second aqueous solution.

5. The method of claim 1 in which an amount of dextrose effective for providing 0 to 50 grams of dextrose per liter of said dialysis solution is present in said second aqueous solution.

6. A product solution consisting essentially of water, calcium chloride and acetic acid and being free of sodium chloride, the concentration of calcium chloride being about 50 to 550 grams per liter and the concentration of acetic acid being about 275 to 475 grams per liter.

7. A product solution consisting essentially of water, calcium chloride and hydrochloric acid and being free of sodium chloride, the concentration of calcium chloride being about 50 to 550 grams per liter and the concentration of hydrochloric acid being about 70 to 90 grams per liter.

8. A product solution consisting essentially of water, calcium chloride and lactic acid and being free of sodium chloride, the concentration of calcium chloride being about 50 to 550 grams per liter and the concentration of lactic acid being about 400 to 700 grams per liter.

9. A product solution consisting essentially of water, calcium chloride, magnesium chloride and acetic acid and being free of sodium chloride, the concentration of calcium chloride being about 50 to 350 grams per liter, the concentration of magnesium chloride being about 0 to 115 grams per liter and the concentration of acetic acid being about 275 to 475 grams per liter.

10. A product solution consisting essentially of water, calcium chloride, magnesium chloride and hydrochloric acid and being free of sodium chloride, the concentration of calcium chloride being about 50 to 350 grams per liter, the concentration of magnesium chloride being about 0 to 115 grams per liter and the concentration of hydrochloric acid being about 70 to 90 grams per liter.

11. A product solution consisting essentially of water, calcium chloride, magnesium chloride and lactic acid and being free of sodium chloride, the concentration of calcium chloride being about 50 to 350 grams per liter, the concentration of magnesium chloride being about 0 to 115 grams per liter and the concentration of lactic acid being about 400 to 700 grams per liter.

12. A substantially water-free particulate admixture product consisting essentially of 40 to 70% by weight sodium chloride, 20 to 40% by weight sodium bicarbonate, 0 to 3% by weight potassium chloride and 0 to 40% by weight dixtrose and being free of calcium and magnesium salts.

13. The substantially water-free particulate admixture product of claim 12 in which the sodium chloride is about 63.5% by weight, the sodium bicarbonate is about 35% by weight and the potassium chloride is about 1.5% by weight of said particulate admixture.

14. The substantially water-free particulate admixture product of claim 12 in which the sodium chloride is about 36% by weight, the sodium bicarbonate is about 24% by weight, the potassium chloride is about 0.85% by weight and the dextrose is about 40% by weight of said particulate admixture.

15. A method of preparing a predetermined volume of a dialysis solution comprising:
   (a) diluting the product solution of any one of claims 6, 7, 8, 9, 10 or 11 with an amount of water effective for forming a first solution having about one-half the volume of said dialysis solution;
   (b) forming a second solution by dissolving a particulate water-free admixture selected from the group consisting of: (i) an admixture free of calcium and magnesium salts and consisting essentially of about 40 to 70% by weight sodium chloride, about 20 to 40% by weight sodium bicarbonate, about 0 to 3% by weight potassium chloride and about 0 to 40% by weight dextrose; (ii) a substantially water-free particulate admixture free of calcium and magnesium salts consisting essentially of about 63.5% by weight sodium chloride, about 35% by weight sodium carbonate and about 1.5% by weight potassium chloride; and (iii) an admixture free of calcium and magnesium salts and consisting essentially of about 36% by weight sodium chloride, about 24% by weight sodium bicarbonate, about 0.85% by weight potassium chloride and about 40% by weight dextrose;
   (c) diluting said second solution with an amount of water effective for a third solution having about one-half the volume of the dialysis solution;
   (d) concurrently admixing said first solution and said third solution to form said dialysis solution; and
   (e) recovering said dialysis solution.

16. A method for preparing a bicarbonate dialysis solution, said dialysis solution consisting essentially of (a) about 120 to 155 m Eq per liter of sodium ion; (b) about 30 to 42 m Eq per liter of bicarbonate ion; (c) about 1 to 5 m Eq per liter of calcium ion; (d) about 0 to 2 m Eq per liter magnesium ion; (e) about 0 to 7 m Eq per liter of acetate ion; (f) about 0 to 3 m Eq per liter of potassium ion; (g) about 0 to 5 grams per liter dextrose; (h) about 80 to 115 m Eq per liter chloride ion; (i) about 0 to 5 m Eq per liter lactate ion; and (j) water to make one liter, said dialysis solution being prepared by admixing water and an acid concentrate consisting essentially of water, calcium chloride, magnesium chloride when required and an amount of acetic acid, hydrochloric or lactic acid effective for causing the dialysis solution to have a pH of 7.2 to 7.4, said acid concentrate being free of sodium chloride, with an aqueous solution consisting of sodium bicarbonate, sodium chloride, potassium chloride when required and dextrose when required and being free of calcium and magnesium salts; the aqueous bicarbonate comprising solution being prepared by admixing with water a substantially water-free particulate admixture consisting essentially of sodium chloride, sodium bicarbonate, potassium chloride when required and dextrose when required.

17. A method for preparing about 2 liters of a solution useful for peritoneal dialysis comprising: (a) packaging: (i) about 45.7 grams of a substantially water-free particulate admixture consisting essentially of 589 parts by weight of sodium bicarbonate, 823 parts by weight of sodium chloride and 2,700 parts by weight of dextrose in a flexible plastic bag; (ii) removing air from said flexible plastic bag, and (iii) sealing the resulting substantially air-free flexible plastic bag; (b) packaging about 1.666 ml of an acidic concentrated aqueous solution consisting essentially of 233 grams of calcium chloride per liter, 85 grams of magnesium chloride per liter and 378 grams of lactic acid per liter in a needle-equipped hypodermic syringe; (c) adding about 2 liters of de-aerated water to the substantially air-free flexible plastic bag without introducing air into the bag, and dissolving said water-free particulate admixture in said water; and (d) transferring the aforesaid acidic concentrated aqueous solution from the hypodermic syringe to the solution in said bag and mixing the resulting composition therein to form said solution useful for peritoneal dialysis.

* * * * *